US009493626B1

(12) United States Patent
Bosnyak et al.

(10) Patent No.: US 9,493,626 B1
(45) Date of Patent: *Nov. 15, 2016

(54) DISPERSIONS COMPRISING DISCRETE CARBON NANOTUBE FIBERS

(71) Applicant: MOLECULAR REBAR DESIGN, LLC, Austin, TX (US)

(72) Inventors: Clive P. Bosnyak, Dripping Springs, TX (US); Kurt W. Swogger, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,215

(22) Filed: Aug. 1, 2016

Related U.S. Application Data

(63) Continuation-in-part of application No. 15/166,931, filed on May 27, 2016, now Pat. No. 9,422,413, which is a continuation of application No. 14/924,246, filed on Oct. 27, 2015, now Pat. No. 9,353,240, which is a continuation of application No. 13/933,206, filed as application No. PCT/EP2011/072427 on Dec. 12, 2011, now Pat. No. 9,212,273.

(60) Provisional application No. 61/423,033, filed on Dec. 14, 2010.

(51) Int. Cl.
C08K 3/04 (2006.01)
C08K 7/06 (2006.01)
C08K 7/24 (2006.01)
B60C 1/00 (2006.01)
C01B 31/02 (2006.01)
C08L 21/02 (2006.01)
C08K 5/00 (2006.01)

(52) U.S. Cl.
CPC ............... C08K 3/04 (2013.01); C08K 5/0008 (2013.01)

(58) Field of Classification Search
CPC ............ C08K 3/04; C08K 7/06; C08K 7/24; C01B 31/02; C01B 31/022; C01B 31/0206; B60C 1/00; C08L 21/02
USPC ................................................. 524/495, 575
See application file for complete search history.

(56) References Cited

U.S. PATENT DOCUMENTS

| | | | |
|---|---|---|---|
| 3,884,606 A | 5/1975 | Schrenk | |
| 7,229,556 B1 | 6/2007 | Hinds, III et al. | |
| 7,453,085 B2 | 11/2008 | Chang et al. | |
| 7,611,628 B1 | 11/2009 | Hinds, III | |
| 7,708,979 B2 | 5/2010 | Lowman et al. | |
| 2003/0096104 A1 | 5/2003 | Tobita et al. | |
| 2003/0144415 A1 | 7/2003 | Wang et al. | |
| 2005/0006623 A1 | 1/2005 | Wong et al. | |
| 2005/0106093 A1 | 5/2005 | Iijima et al. | |
| 2006/0286456 A1 | 12/2006 | Fu et al. | |
| 2007/0125707 A1 | 6/2007 | Komatsu et al. | |
| 2007/0215841 A1 | 9/2007 | Ford et al. | |
| 2007/0244263 A1 | 10/2007 | Burrowes | |
| 2007/0259994 A1* | 11/2007 | Tour | B82Y 30/00 523/333 |
| 2007/0280876 A1 | 12/2007 | Tour et al. | |
| 2008/0090951 A1 | 4/2008 | Mao et al. | |
| 2008/0102020 A1 | 5/2008 | Niu et al. | |
| 2008/0220148 A1 | 9/2008 | Clarkson et al. | |
| 2008/0262126 A1 | 10/2008 | Fleischer et al. | |
| 2008/0290007 A1 | 11/2008 | Fagan et al. | |
| 2008/0299374 A1 | 12/2008 | Choi et al. | |
| 2008/0312364 A1 | 12/2008 | Piccione et al. | |
| 2009/0030105 A1 | 1/2009 | Miyasaka et al. | |
| 2009/0038858 A1 | 2/2009 | Griffo et al. | |
| 2009/0169876 A1 | 7/2009 | Yamamoto et al. | |
| 2009/0171768 A1 | 7/2009 | Chopra et al. | |
| 2009/0311489 A1 | 12/2009 | Sheehan et al. | |
| 2010/0004468 A1 | 1/2010 | Wong et al. | |
| 2010/0098877 A1 | 4/2010 | Cooper et al. | |
| 2010/0201023 A1 | 8/2010 | Piccione et al. | |
| 2010/0215724 A1 | 8/2010 | Prakash et al. | |
| 2010/0258238 A1 | 10/2010 | Hoover et al. | |
| 2010/0324315 A1 | 12/2010 | Atyabi et al. | |
| 2011/0311876 A1 | 12/2011 | Sturgeon et al. | |
| 2012/0183770 A1 | 7/2012 | Bosnyak et al. | |
| 2012/0329640 A1 | 12/2012 | Bosnyak et al. | |
| 2013/0178722 A1 | 7/2013 | Aria et al. | |
| 2015/0182473 A1 | 7/2015 | Bosnyak et al. | |

(Continued)

FOREIGN PATENT DOCUMENTS

| | | |
|---|---|---|
| EP | 1061040 A1 | 12/2000 |
| EP | 2241522 A2 | 10/2010 |

(Continued)

OTHER PUBLICATIONS

Bhattacharyya et al., "Improving reinforcement of natural rubber by networking of activated carbon nanotubes", Carbon 46(2008) 1037-1045.*
Dyke, et al., "Solvent-free functionalization of carbon nanotubes", 125 J. Am. Chem. Soc. (2003), p. 1156-1157.
Aviles et al., "Evaluation of Mild Acid Oxidation Treatments for MWCNT Functionalization", 47 Carbon (2009), pp. 2970-2975.
Bhattacharyya et al., "Improving reinforcement of natural rubber by networking of activated carbon nanotubes" 46 Carbon (2008), pp. 1037-145.
Sui et al., "Curing kinetics and mechanical behavior of natural rubber reinforced with pretreated carbon nanotubes", 485 Materials Sci.. & Eng. A (2008), pp. 524-531.

(Continued)

Primary Examiner — Ling Choi
Assistant Examiner — Ronald Grinsted

(57) ABSTRACT

This present invention relates to the carbon nanotubes as composites with materials such as elastomers, thermosets and thermoplastics or aqueous dispersions of open-ended carbon nanotubes with additives. A further feature of this invention relates to the development of a concentrate of carbon nanotubes with an elastomer wherein the concentrate can be further diluted with an elastomer and other polymers and fillers using conventional melt mixing equipment.

20 Claims, No Drawings

(56) References Cited

U.S. PATENT DOCUMENTS

2015/0238476 A1 8/2015 Bosnyak et al.
2016/0095940 A1 4/2016 Swogger et al.

FOREIGN PATENT DOCUMENTS

| | | |
|---|---|---|
| EP | 1665446 B1 | 3/2012 |
| FR | 2887554 A1 | 12/2006 |
| JP | 2004101958 A | 4/2004 |
| JP | 2004210830 A | 7/2004 |
| JP | 2005-334594 A | 12/2005 |
| JP | 2006-240901 | 9/2006 |
| JP | 2007516314 | 6/2007 |
| JP | 2009534284 | 9/2009 |
| KR | 20090108426 A | 10/2009 |
| WO | 03060002 A1 | 7/2003 |
| WO | 2004106420 A1 | 12/2004 |
| WO | 2005014708 A1 | 2/2005 |
| WO | 2006096613 A1 | 9/2006 |
| WO | 2007119231 A1 | 10/2007 |
| WO | 2008011623 A1 | 1/2008 |
| WO | 2008051239 A1 | 5/2008 |
| WO | 2008112362 A2 | 9/2008 |
| WO | 2008153609 A1 | 12/2008 |
| WO | 2009155267 A1 | 12/2009 |
| WO | 2010087971 A2 | 8/2010 |
| WO | 2010117392 A1 | 10/2010 |
| WO | 2012083358 A1 | 6/2012 |
| WO | 2013011516 A1 | 1/2013 |
| WO | 2013090844 A1 | 6/2013 |

OTHER PUBLICATIONS

Goyanes et al., "Carboxylation treatment of multiwalled carbon nanotubes monitored by infrared and ultraviolet spectroscopies and scanning probe microscopy:", 16 Diamond & Related Materials (2007), pp. 412-417.
Nanocyl, Nanocyl NC3100 Series Product Information Sheet: http://www.nanocyl.com/en/Products-Solutions/Products/Research-Grades/Thin-Multi-Wall-Carbon-Nanotubes (May 29, 2012).
Shanmugharaj et al., "Physical and chemical characteristics of multiwalled carbon nanotubes functionalized with aminosilane and its influence on the properties of natural rubber composites", 67(9) Compos. Sci. & Tech. (2007), pp. 1813-1822.
Defalco et al., "Carbon nanotubes as reinforcement of styrene-butadiene rubber", 254(1) Appl. Surface Sci. (2007), pp. 262-265.
Zhou et al., "Polypropylene composites having carbon nanotubes and powder styrene-butadiene rubber", Instit. of Electr. Eng., Steveage, GB (2008).
Zhou et al., "New Fabrication and Mechanical Properties of Styrene-Butadiene Rubber/Carbon Nanotubes Nanocomposite", 26(12) J. Mater. Sci. & Tech. (2010), pp. 1127-1132.
Tchoul et al., "Effect of Mild Nitric Acid Oxidation on Dispersability, Size, and Structure of Single-Walled Carbon Nanotubes", 10 Chem. Mater. (2007), pp. 5765-5772.
Xing et al., "Sonochemical Oxidation of Multiwalled Carbon Nanotubes", 21 Langmuir (2005), pp. 4185-4190.
Spitalsky, Z., et al., "High Volume Fraction Carbon Nanotube-Epoxy Composites", Nanotechnology, vol. 20, No. 40, Oct. 7, 2009.
Kim, Hee-Cheul, et al., "The Effect of Different Treatment Methods of Multiwalled Carbon Nanotubes on Thermal and Flexural Properties of Their Epoxy Nanocomposites", Journal of Polymer Science: Part B: Polymer Physics, vol. 48, No. 11, Jun. 1, 2010.
Hadjiev, V.G., et al., "Raman Microscopy of Residual Strains in Carbon Nanotube/Epoxy Composites", Carbon, vol. 48, No. 6, May 1, 2010.
Lee, J.H., et al., "Effects of Moisture Absorption and Surface Modification Using 3-Aminopropyltriethoxysilane on the Tensile and Fracture Characteristics of MWCNT/Epoxy Nanocomposites", Applied Surface Science, vol. 256, No. 24, Jun. 15, 2010.
Zhu, Jiang, et al., "Improving the Dispersion and Integration of Single-Walled Carbon Nanotubes in Epoxy Composites Through Functionalization", Nano Letters, vol. 3, No. 8, Aug. 1, 2003.
Liu, L., et al., "Rubbery and Glassy Epoxy Resins Reinforced With Carbon Nanotubes", Composites Science and Technology, vol. 65, No. 11-12, Sep. 1, 2005.
Chen, Wei, et al., "Carbon Nanotube-Reinforced Polyurethane Composite Fibers", Composites Science and Technology, vol. 66, No. 15, Dec. 1, 2006.
Wu, Guoliang, et al., "Preparation and Properties of Hydroxylated Styrene-Butadiene-Styrene Tri-Block Copolymer Imulti-Walled Carbon Nanotubes Nanocomposites Via Covalent Bond", Materials Science and Engineering; vol. 527, No. 20, May 6, 2010.
Barroso-Bujans, F., et al., "Effects of Functionalized Carbon Nanotubes in Peroxide Crosslinking of Diene Elastomers", European Polymer Journal, vol. 45, No. 4, Apr. 1, 2009.
Zhou, Xiang-Wen, et al., "Preparation and Properties of Powder Styrene-Butadiene Rubber Composites Filled With Carbon Black and Carbon Nanotubes", Materials Research Bulletin, vol. 42, No. 3, Feb. 22, 2007.
Vast, L., et al., "Preparation and Electrical Characterization of a Silicone Elastomer Composite Charged With Multi-Wall Carbon Nanotubes Functionalized With 7-Octenyltrichlorosilane", Composites Science and Technology, vol. 67, No. 5, Jan. 18, 2007.
Broza, Georg, et al., "Thermoplastic Elastomers With Multi-Walled Carbon Nanotubes: Influence of Dispersion Methods on Morphology", Composites Science and Technology; vol. 70, No. 6, Jun. 1, 2010.
Chen, Shuguo, et al., "Thermal Degradation Behavior of Hydrogenated Nitrile-Butadiene Rubber (HNBR) / Clay Nanocomposite and HMBR / Clay/ Carbon Nanotube Nanocomposites", Thermochimica Acta; vol. 491, No. 1-2, Jul. 20, 2009.
Bokobza, "Multiwall Carbon Nanotube Elastomeric Composites; A Review", Polymer, vol. 48, No. 17, Aug. 3, 2007.
Zhang et al., Effect of Chemical Oxidation on the Sturcture of Single-Walled Carbon Nanotubes, 107(16) J. Phys. Chem. B (2003), pp. 3712-3718.
Press Release—"Biopact Launches R&D Kits in Philadelphia at Bio Conference", retrieved from Biopact.com (2016).
Yoong et al., "Enhanced cytotoxicity to cancer cells by mitochondria-targeting MWCNTs containing platinum(IV) prodrug of cisplatin", 35(2) Biomaterials (Oct. 18, 2013), pp. 748-759.
Luo et al., "Carbon nanotube nanoreservoir for controlled release of anti-inflammatory dexamethasone", 32(26) Elsevier Science Publishers BV, Barking GB (2011), pp. 6316-6323.
Wu et al., "PEGylated multi-walled carbon nanotubes for encapsulation and sustained release of oxaliplatin" 30(2) Pharmaceutical Research (2012), pp. 412-423.
Wu et al., "Trojan-Horse Nanotube On-Command Intracellular Drug Delivery", 12(11) Nano Letters (2012), pp. 5475-5480.
Raoof et al., "Remotely triggered cisplatin release from carbon nanocapsules by radiofrequency fields", 34(7) Biomatenals (2013), pp. 1862-1869.
Ahmed et al., "Adsorption-Desorption Behavior of Polyvinyl Alcohol on Polystyrene Latex Particles", ACS Symp. Series 240 (1983), pp. 77-94.
Danielsson, J.,"NMR Studies of the amylois b-peptide" Ph.D. Thesis, Stockholm University (2007).
Mashat et al., "Zippered release from polymer-gated carbon nanotubes", 22 J. Mater. Chem. (2012), pp. 11503-11508.
Shen et al., Polyethyeneimine-Mediated Functionalization of Multiwalled Carbon Nanotubes: Synthesis, Characterization, and In Vitro Toxicity Assay, 113(8) J. Phys. Chem. C (2009), pp. 3150-3156.
Rosca et al., "Oxidation of multiwalled carbon nanotubes by nitric acid", 43(15) Carbon (2005), pp. 3124-3131.
Ziebacz et al., "Crossover regime for diffusion of nanoparticles in polyethylene glycol solutions: influence of depletion layer", Electronic Supp. Mat. (ESI) for Soft Matter, Royal Soc. Chem. (2011), pp. 1-10.
Kovtyukhova et al., Individual Single-Walled Nanotubes and Hydrogels Made by Oxidative Exfoliation of Carbon Nanotube Ropes, 125 J. Amer. Chem. Soc. (2003, pp. 9761.

(56) References Cited

OTHER PUBLICATIONS

Andrews et al., "Continuous Production of Aligned Carbon Nanotubes: A Step Closer to Commercial Realization", 303 Chem. Phys. Let. 467 (1999).

Margetts et al., "Transdermal drug delivery: principles and opoid therapy", 7(5) Oxford Journal, Medicine BJA: CEACCP (2007), pp. 171-176.

\* cited by examiner

DISPERSIONS COMPRISING DISCRETE CARBON NANOTUBE FIBERS

CROSS-REFERENCES

This application is a continuation-in-part application of U.S. Ser. No. 15/166,931 filed May 27, 2016 and allowed Jul. 7, 2016 which was a continuation of U.S. Ser. No. 14/924,246, filed Oct. 27, 2015 and issued as U.S. Pat. No. 9,353,240, which is a continuation of U.S. Ser. No. 13/993, 206, filed Jun. 11, 2013 and issued as U.S. Pat. No. 9,212, 273, which claims priority to PCT/EP2011/072427, filed Dec. 12, 2011, which claims benefit of U.S. provisional application 61/423,033, filed Dec. 14, 2010. This application is also related to U.S. Ser. Nos. 14/585,730; 14/628,248; and 14/963,845.

FIELD OF INVENTION

The present invention is directed to novel compositions and methods for producing elastomer composite blends with discrete carbon nanotubes.

BACKGROUND OF THE INVENTION

Carbon nanotubes can be classified by the number of walls in the tube, single-wall, double wall and multiwall. Each wall of a carbon nanotube can be further classified into chiral or non-chiral forms. Carbon nanotubes are currently manufactured as agglomerated nanotube balls or bundles. Use of carbon nanotubes as a reinforcing agent in polymer composites is an area in which carbon nanotubes are predicted to have significant utility. However, utilization of carbon nanotubes in these applications has been hampered due to the general inability to reliably produce individualized carbon nanotubes. To reach the full potential of performance enhancement of carbon nanotubes as composites in polymers the aspect ratio, that is length to diameter ratio, should be substantially greater than 40. The maximum aspect ratio for a given tube length is reached when each tube is fully separated from another. A bundle of carbon nanotubes, for example, has an effective aspect ratio in composites of the average length of the bundle divided by the bundle diameter.

Various methods have been developed to debundle or disentangle carbon nanotubes in solution. For example, carbon nanotubes may be shortened extensively by aggressive oxidative means and then dispersed as individual nanotubes in dilute solution. These tubes have low aspect ratios not suitable for high strength composite materials. Carbon nanotubes may also be dispersed in very dilute solution as individuals by sonication in the presence of a surfactant. Illustrative surfactants used for dispersing carbon nanotubes in aqueous solution include, for example, sodium dodecyl sulfate, or cetyltrimethyl ammonium bromide. In some instances, solutions of individualized carbon nanotubes may be prepared from polymer-wrapped carbon nanotubes. Individualized single-wall carbon nanotube solutions have also been prepared in very dilute solutions using polysaccharides, polypeptides, water-soluble polymers, nucleic acids, DNA, polynucleotides, polyimides, and polyvinylpyrrolidone. The dilution ranges are often in the mg/liter ranges and not suitable for commercial usage.

SUMMARY OF THE INVENTION

The present invention relates to a composition comprising a plurality of discrete carbon nanotube fibers having an aspect ratio of from about 25 to about 500, and at least one natural or synthetic elastomer, and optionally at least one filler. The composition can have carbon nanotube fibers with an oxidation level of from about 3 weight percent to about 15 weight percent, or from about 0.5 weight percent up to about 4, or up to about 3, or up to 2 weight percent based on the total weight of discrete carbon nanotubes. The carbon nanotube fibers comprise preferably of about 1 weight percent to about 30 weight percent of the composition and the composition is in the form of free flowing particles or a bale. The composition is further comprising of at least one surfactant or dispersing aid. The composition can comprise the natural or synthetic elastomer selected from the group consisting of, but not limited to, natural rubbers, polyisobutylene, polybutadiene and styrene-butadiene rubber, butyl rubber, polyisoprene, styrene-isoprene rubbers, styrene-isoprene rubbers, ethylene propylene diene rubbers, silicones, polyurethanes, polyester-polyethers, hydrogenated and non-hydrogenated nitrile rubbers, halogen modified elastomers, flouro-elastomers, and combinations thereof. The composition contains fibers that are not entangled as a mass and are uniformly dispersed in the elastomer.

In another embodiment, the invention is a process to form a carbon nanotube fiber/elastomer composite comprising the steps of: (a) selecting discrete carbon nanotube fibers having an aspect ratio of from 25 to 500, (b) blending the fibers with a liquid to form a liquid/fiber mixture, (c) optionally adjusting the pH to a desired level, (d) agitating the mixture to a degree sufficient to disperse the fibers to form a dispersed fiber mixture, (e) optionally combining the dispersed fiber mixture with at least one surfactant, (f) combining the dispersed fiber mixture with at least one elastomer at a temperature sufficient to incorporate the dispersed fiber mixture to form a carbon nanotube fiber/elastomer composite/liquid mixture, (g) isolating the resulting carbon nanotube fiber/elastomer composite from the liquid. The carbon nanotube fibers comprise from about 1 to about 30 weight percent of the fiber/elastomer composite of (g). The liquid is aqueous based. The agitating step (d) comprises sonication. In this embodiment, the elastomer is selected from, but not limited to, the natural or synthetic elastomer selected from the group consisting of, but not limited to, natural rubbers, polyisobutylene, polybutadiene and styrene-butadiene rubber, butyl rubber, polyisoprene, styrene-isoprene rubbers, styrene-isoprene rubbers, ethylene propylene diene rubbers, silicones, polyurethanes, polyester-polyethers, hydrogenated and non-hydrogenated nitrile rubbers, halogen modified elastomers, fluoro-elastomers, and combinations thereof. The composition is further comprising sufficient natural or synthetic elastomer to form a formulation comprising from about 0.1 to about 25 weight percent carbon nanotube fibers.

In another embodiment, the invention is a formulation in the form of a molded or fabricated article, such as a tire, a hose, a belt, a seal and a tank track pad, wheel, bushings or backer plate components.

In another embodiment, the invention is a nanotubes/elastomer composite further comprising of filler or fillers such as carbon black and/or silica, and wherein a molded film comprising the composition has a tensile modulus at 5 percent strain of at least about 12 MPa. The composition comprising of carbon black, and wherein a molded film comprising the composition has a tear property of at least about 0.8 MPa.

In yet another embodiment of the invention is a carbon nanotube/elastomer composition further comprising of filler, and where in a molded film comprising the composition has a tensile modulus at 5% strain of at least 8 MPa.

In yet another embodiment of the invention is a carbon nanotube fiber/elastomer composite, wherein the carbon nanotube fibers are discrete fibers and comprise from about 10 to about 20 weight percent fibers and wherein the elastomer comprises a styrene copolymer rubber.

In still another embodiment of the invention is a method for obtaining individually dispersed carbon nanotubes in rubbers and/or elastomers comprising (a) forming a solution of exfoliated carbon nanotubes at pH greater than or equal to about 7, (b) adding the solution to a rubber or elastomer latex to form a mixture at pH greater than or equal to about 7, (c) coagulating the mixture to form a concentrate, (d) optionally incorporating other fillers into the concentrate, and (e) melt-mixing said concentrate into rubbers and/or elastomers to form elastomeric composites. In this embodiment the carbon nanotubes comprise less than or equal to about 2 percent by weight of the solution. A further embodiment is that the coagulation step comprises mixing with acetone. In another embodiment, the coagulation step comprises drying the mixture. In yet another embodiment the coagulation step comprises adding at least one acid to the mixture at pH less than or equal to about 4.5 together with at least one monovalent inorganic salt. In another embodiment, the mixture has divalent or multivalent metal ion content of less than about 20,000 parts per million, preferably less than about 10,000 parts per million and most preferably less than about 1,000 parts per million.

Another aspect of this invention are coagulating methods/agents are those that enable the carbon nanotube to be non-ordered on the surface of the elastomer latex particle and together are substantially removable from the liquid mixture. A further aspect of this invention is a method to reduce or remove surfactants in the latex/carbon nanotube fiber composite system organic molecules of high water solubility such as acetone, denatured alcohol, ethyl alcohol, methanol, acetic acid, tetrahydrofuran. Another aspect of this invention is to select coagulating methods that retain surfactant in the latex/carbon nanotube fiber material which includes coagulating methods such as sulfuric acid and inorganic monovalent element salt mixtures, acetic acid and monovalent element salt mixtures, formic acid and inorganic monovalent element salt mixtures, air drying, air spraying, steam stripping and high speed mechanical agitation.

Yet another embodiment of the invention is an individually dispersed carbon nanotube/rubber or carbon nanotube/elastomer concentrate comprising free flowing particles or a bale. A further aspect of this invention is an individually dispersed carbon nanotube/rubber or carbon nanotube/elastomer concentrate comprising free flowing particles or a bale wherein the concentrate contains a concentration of less than 20,000 parts per million of divalent or multivalent metal salt.

Another embodiment of the invention is an individually dispersed carbon nanotube/rubber or carbon nanotube/elastomer concentrate comprising free flowing particles or a bale wherein the concentrate contains agglomerations of carbon nanotubes that comprise less than 1 percent by weight of the concentrate and wherein the carbon nanotube agglomerates comprise more than 10 microns in diameter. An embodiment of the invention is a composite comprising the concentrate.

In another embodiment, the elastomer nanotube fiber composition, particularly materials made from elastomers commonly called either natural or synthetic rubber or rubber compounds (with the addition of fillers such as carbon or silicon) includes wherein the fiber surface modifier or surfactant is chemically or physically (or both) bonded to the elastomer and/or the isolated fibers or the filler in the compounds.

In another embodiment, the material-nanotube fiber composition includes wherein the fiber surface modifier or surfactant is chemically bonded to the material and/or fiber. As an example, oleylamine (1-amino-9-octadecene) can be reacted, with carbon nanotubes containing carboxylic groups to give the amide. On addition of the amide modified carbon nanotube fiber to a vinyl containing polymer material such as styrene-butadiene followed by addition of crosslinking agents comprising such as peroxides or sulfur, the vinyl containing polymer can be covalently bonded to the amide functionality of the carbon nanotube.

In one embodiment of this invention a method is disclosed in which the elastomer/carbon nanotube concentrate is dispersed first into another elastomer or thermoplastic to a uniform consistency before addition of other additives such as other fillers and additives, including carbon black, silica, graphene, oils and antioxidants.

Another embodiment of this invention is a method of mixing carbon nanotubes and at least one first elastomer, wherein a master batch of carbon nanotubes is first melt mixed with the elastomer, either the same or different from the first elastomer, at a temperature from about 20 to about 200° C., subsequently then additional elastomers, fillers, and additives are added and melt mixed further, to produce a composition suitable for vulcanization. A solvent can be added to facilitate mixing which can be removed after the at least one first elastomer, wherein a master batch of carbon nanotubes is first mixed with the elastomer, or after all ingredient are added and mixed.

The exfoliated carbon nanotube fibers of this invention impart significant strength and stiffness to the materials. These new elastomer nanotube filler materials can improve the frictional, adhesive, cohesive, noise and vibration, rolling resistance, tear, wear, fatigue and crack resistance, hysteresis, large strain effects (Mullins effect), small strain effects (Payne effect) and oscillation or frequency properties and swelling resistance to oil of the elastomers and elastomer compounds. This change in properties will be beneficial for applications such as tires or other fabricated rubber or rubber compounded parts.

For a more complete understanding of the present disclosure, and the advantages thereof, reference is now made to the following descriptions describing specific embodiments of the disclosure.

DETAILED DESCRIPTION OF THE INVENTION

In the following description, certain details are set forth such as specific quantities, sizes, etc., so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

Functionalized carbon nanotubes of the present disclosure generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof. In some embodiments, the carbon nanotubes may be functionalized before, during and after being exfoliated.

In various embodiments, a plurality of carbon nanotubes is disclosed comprising single wall, double wall or multi wall carbon nanotube fibers having an aspect ratio of from about 25 to about 500, preferably from about 60 to about 200, and a oxidation level of from about 3 weight percent to about 15 weight percent, preferably from about 5 weight percent to about 10 weight percent. The oxidation level is defined as the amount by weight of oxygenated species covalently bound to the carbon nanotube. The thermogravimetric method for the determination of the percent weight of oxygenated species on the carbon nanotube involves taking about 5 mg of the dried oxidized carbon nanotube and heating at 5° C./minute from room temperature to 1000 degrees centigrade in a dry nitrogen atmosphere. The percentage weight loss from 200 to 600 degrees centigrade is taken as the percent weight loss of oxygenated species. The oxygenated species can also be quantified using fourier transform infra-red spectroscopy, FTIR, particularly in the wavelength range 1730-1680 $cm^{-1}$.

The carbon nanotube fibers can have oxidation species comprising of carboxylic acid or derivative carbonyl containing species and are essentially discrete individual fibers, not entangled as a mass. The derivative carbonyl species can include ketones, quaternary amines, amides, esters, acyl halogens, monovalent metal salts and the like.

As-made carbon nanotubes using metal catalysts such as iron, aluminum or cobalt can retain a significant amount of the catalyst associated or entrapped within the carbon nanotube, as much as five weight percent or more. These residual metals can be deleterious in such applications as electronic devices because of enhanced corrosion or can interfere with the vulcanization process in curing elastomer composites. Furthermore, these divalent or multivalent metal ions can associate with carboxylic acid groups on the carbon nanotube and interfere with the discretization of the carbon nanotubes in subsequent dispersion processes. In other embodiments, the oxidized fibers comprise a residual metal concentration of less than about 10000 parts per million, ppm, and preferably less than about 1000 parts per million. The metals can be conveniently determined using energy dispersive X-ray, EDX.

In another embodiment, a mixture of master batches using different rubbers added to blends of different rubbers used in the rubber compound such that each rubber has a master batch that is compatible so that the individually dispersed nanotubes are distributed whether uniformly or non-uniformly in each rubber domain. This is sometimes necessary so that blends of rubbers used in the rubber compound will have carbon nanotubes in each rubber component.

An illustrative process for producing discrete oxidized carbon nanotubes follows: 3 liters of sulfuric acid, 97 percent sulfuric acid and 3 percent water, and 1 liter of concentrated nitric acid containing 70 percent nitric acid and 3 percent water, are added into a 10 liter temperature controlled reaction vessel fitted with a sonicator and stirrer. 40 grams of non-discrete carbon nanotubes, grade Flowtube 9000 from CNano corporation, are loaded into the reactor vessel while stirring the acid mixture and the temperature maintained at 30° C. The sonicator power is set at 130-150 watts and the reaction is continued for three hours. After 3 hours the viscous solution is transferred to a filter with a 5 micron filter mesh and much of the acid mixture removed by filtering using a 100 psi pressure. The filter cake is washed one times with four liters of deionized water followed by one wash of four liters of an ammonium hydroxide solution at pH greater than 9 and then two more washes with four liters of deionized water. The resultant pH of the final wash is 4.5. A small sample of the filter cake is dried in vacuum at 100° C. for four hours and a thermogravimetric analysis taken as described previously. The amount of oxidized species on the fiber is 8 percent weight and the average aspect ratio as determined by scanning electron microscopy to be 60.

The discrete oxidized carbon nanotubes (CNT) in wet form are added to water to form a concentration by weight of 1 percent and the pH is adjusted to 9 using ammonium hydroxide. Sodium dodecylbenzene sulfonic acid and is added at a concentration 1.25 times the mass of oxidized carbon nanotubes. The solution is sonicated while stirring until the CNT are fully dispersed in the solution. Full dispersion of individual tubes is defined when the UV absorption at 500 nm is above 1.2 absorption units for a concentration of $2.5 \times 10^{-5}$ g CNT/mL Latex SBR LPF 5356 (Goodyear Rubber Company) with a solids SBR concentration of 70.2% (by weight) was added to the CNT solution such that the solids ratio is 10 parts CNT for 90 parts SBR by weight.

Sulfuric acid is then added sufficient to bring the pH to 2 and sodium chloride added at a ratio of 50 g/liter of fluid while stirring. Stirring continues for 10 minutes then the coagulant is removed by filtering. The filtrate is a clear liquid. The coagulant is dried in a vacuum oven at 40° C. overnight.

Preparation of Aqueous Dispersions Comprising Additives According to the Present Invention As described above and below, various additives may be employed in the aqueous dispersions of discrete, multi-wall oxidized carbon nanotubes. If desired, the carbon nanotubes may be open on at least one or both ends. In this manner at least a portion of the additives that are appropriate in size may be contained in the interior of the discrete multi-wall carbon nanotubes. Typically, the average diameter of the multi-wall nanotube opening is larger than the hydrodynamic radius of the additive molecules to be contained within the interior of the discrete, multi-wall oxidized carbon nanotubes. Such average diameters of the multi-wall nanotube opening will vary by specific carbon nanotubes but may be at least about 1, or at least about 3, up to about 15, or up to about 8 nanometers. Typically, representative additive molecules that fit within representative discrete, multi-wall oxidized carbon nanotubes are less than 50,000 Daltons, or less than 40,000, or less than 30,000, or less than 25,000, or less than 20,000 or even less than 17,000 Daltons.

Such additives may include, for example, various surfactants or dispersing aids and compounds such as sodium dodecyl sulfate, cetyltrimethyl ammonium bromide, polyvinyl alcohol, polyalkylene oxide such as polyethylene oxide, cellulosics such as carboxymethyl cellulose, polyacids such as polyglycolic acid, polyacrylic acid, and polylactic acid, polyvinylpyrrolidone, various peptides and amino acids, as well as proteins, polysaccharides, combinations thereof and the like. Other additives include, for example, drugs, proteins and compounds such as those described in US 2009/0170768 to Tour et al. which is incorporated herein by reference. Exemplary additives include, for example, a drug molecule, a protein molecule, and combinations thereof. Compounds such as a radiotracer molecule, a radiotherapy molecule, a diagnostic imaging molecule, a fluorescent tracer molecule, and combinations thereof may also be added. And as described in Tour US 2009/0170768 others may "include, but are not limited to, proton pump inhibitors, H2-receptor antagonists, cytoprotectants, prostaglandin analogues, beta blockers, calcium channel blockers, diuretics, cardiac glycosides, antiarrhythmics, antianginals, vasoconstrictors, vasodilators, ACE inhibitors, angiotensin receptor blockers, alpha blockers, anticoagulants, antiplatelet drugs, fibrinolytics, hypolipidemic agents, statins, hypnotics, antipsychotics, antidepressants, monoamine oxidase inhibitors, selective serotonin reuptake inhibitors, antiemetics, anticonvulsants, anxiolytic, barbiturates, stimulants, amphetamines, benzodiazepines, dopamine antagonists, antihistamines, cholinergics, anticholinergics, emetics, cannabinoids, 5-HT antagonists, NSAIDs, opioids. bronchodilator, antiallergics, mucolytics, corticosteroids, beta-receptor antagonists, anticholinergics, steroids, androgens, antiandrogens, growth hormones, thyroid hormones, anti-thyroid drugs, vasopressin analogues, antibiotics, antifungals, antituberculous drugs, antimalarials, antiviral drugs, antiprotozoal drugs, radioprotectants, chemotherapy drugs, cytostatic drugs, and cytotoxic drugs. In various embodiments of the compositions, the at least one type of payload molecule comprises paclitaxel."

The amount of additive to be included with the dispersion (aqueous or non-aqueous) or other composition of discrete, multi-wall oxidized carbon nanotubes will vary depending upon the specific additive, the specific carbon nanotubes, desired effect, and other parameters. Typically, the amount of additive is such that greater than about 10, or greater than about 20, or greater than about 25, or greater than about 30, or greater than about 40, or greater than about 50, or greater than about 55, or greater than about 60, or greater than about 70, or greater than about 80, or greater than about 99 weight percent of the additive is within the interior of the discrete, multi-wall oxidized carbon nanotubes that are open on at least one or both ends based on the total weight of additive in the composition or dispersion. Similarly, the weight percent of nanotubes in the dispersion or composition is often low based on the total weight of the dispersion or composition, e.g., from about 0.01, or 0.1, or 0.3, or 0.5, or 0.6 up to about 30, or 15, or 10, or 5 or 3, or 1 weight percent.

Preparation of the Vulcanizable Composition According to the Present Invention:

A further object of the invention resides in the preparation of the vulcanizable compositions, wherein the elastomer, the concentrate of carbon-nanotubes in an elastomer composition and the cross-linking agent and optionally any of the other ingredients of the composition are mixed together. Typically the mixing is performed at an elevated temperature that may range from about 20° C. to about 200° C. The mixing may further be performed in the presence of a solvent which is then removed after mixing.

Normally the mixing time does not exceed one hour and a time in the range from 2 to 30 minutes is usually adequate.

The mixing is suitably carried out in a blending apparatus, e.g. an internal mixer such as a Banbury mixer, or a Haake or Brabender miniature internal mixer. A two roll mill mixer also provides a good dispersion of the carbon-nanotubes as well as of the other optional additives within the elastomer. An extruder also provides good mixing, and permits shorter mixing times. It is possible to carry out the mixing in two of more stages, and the mixing can be done in different apparatus, for example one stage in an internal mixer and one stage in an extruder. However, it should be taken care that no unwanted pre-crosslinking (=scorch) occurs during the mixing stage.

The compounding and vulcanization may be performed as known to any artisan (see e.g. Encyclopedia of Polymer Science and Engineering, Vol. 4, p. 66 et seq. (Compounding) and Vol. 17, p. 666 et seq. (Vulcanization)). Typically such vulcanization is performed at a temperature in the range of from 100 to 200° C., preferably 130 to 180° C. In one embodiment the preparation of a polymer vulcanizate comprises subjecting the inventive composition to a vulcanization during injection or extrusion molding.

Following is an example using styrene butadiene as an elastomer with addition of carbon nanotubes of this invention.

Example 1

The SBR concentrate is melt mixed with additional SBR (Lanxess VSL-5052-OHM) to give a final CNT concentration of 2 percent weight in a Brabender mixer by the following procedure. The temperature of the barrel is set to 115° C. The SBR and master batch is introduced into the barrel at a speed of 20-30 rpm. The speed is then increased to 50 rpm. Barrel temperature should reach 125° C. When the torque has reached a constant value, the speed is decreased to 5 rpm and the temperature controller is turned off. When the temperature in the barrel is 95° C., the speed is increased to 50 rpm. The cure package is added and mixing continues for 5 minutes. The cure package consists of sulfur 3.5 parts per hundred resin, phr, tetrabutylbenzothiozolsulfonamide 0.75 phr, diphenylguanidine 0.5 phr, stearic acid 1.5 phr, N-(1,3 Dimethylbutyl) N'-phenyl-p-phenyldiamine 2 phr and zinc oxide 3 phr.

A comparative 1 is made as above with the exception that no SBR concentrate is added.

The mixture is then cured under the following procedure using a compression molder. The platten temperature is set to 160° C., the curing overall time to 20 minutes and the water cooling time to 5 minutes. A mass of 40.6 g of rubber sample is cut into small ¼" pieces and placed in the center of mold window such that it forms a square, occupying ⅔ of the space. Foil sheets are used between sample and compression plates. Mold release is only used on the mold frame. The sample is compressed with pressure less than 10 psi for 2 minutes. Then, the pressure is increased to 25 tons and kept constant for the remaining curing cycle.

After curing the films are tested in tension at 25° C. using a tensile tester with an initial strain rate of $1 \times 10^{-2}$ s$^{-1}$. Engineering Stress is the load divided by the initial cross-sectional area of the specimen. Strain is defined as the distance traversed by the crosshead of the instrument divided by the initial distance between the grips. The 100% modulus is that value of tensile stress at 100% strain. The films are also tested for work done to completely tear the specimen by introducing a razor edge notch of dimension one half the width and perpendicular to the length of the specimen to a tensile specimen.

TABLE 1

Tensile properties of cured SBR without carbon nanotubes (Comp. Ex. 1)
and SBR with discrete carbon nanotubes (Ex. 1)

| Sample | Tensile Strength (MPa) | 100% Modulus (MPa) | Work done to Tear (MPa) |
|---|---|---|---|
| Comparative 1 SBR | 1.1 | 0.51 | 0.46 |
| Example 1 SBR + 2% wt CNT | 2.26 | 0.8 | 0.79 |

Seen in Table 1, significant improvements in the values of tensile strength, 100% modulus and work done to tear are gained using 2 percent weight of the carbon nanotubes of this invention. These attributes are important elements that will lead to improved wear in elastomer composites.

In another aspect of this invention is a preferred method of mixing that results in improved properties wherein the master batch of carbon nanotubes is first melt mixed with another elastomer then additional rubbers, fillers and additives are added and melt mixed further to produce a composition suitable for vulcanization.

Following is an Example of Preferred Mixing

A comparative example 2 is produced using 3 phr carbon nanotubes of this invention, and carbon black filled rubber system consisting of 3 melt passes. The first pass was to mix the rubber components 60 phr styrene butadiene, SBR Lanxess VSL-5025-OHM and 40 phr Natural Rubber CB 60 grade, and an SBR-carbon nanotubes master batch containing 10 weight percent carbon nanotubes at about 160° C. The second pass was to mix into the first pass products 50 phr carbon black, type N330, 5 phr processing oil Sundex 8125, 1 phr antioxidant 6 PPD Santoflex, 3 phr zinc oxide and 3 phr stearic acid at about 160° C. The third pass was to mix in the sulfur curing compounds 1.5 phr sulfur and 1.3 phr TBBS at about 110° C. Each pass was performed with a fill factor of 75% using a Brabender mixer.

Example 2

The improved mixing approach is the same as the control except the first pass is mixing the SBR with the carbon nanotubes master batch for 5 minutes at about 170° C. followed by adding the natural rubber at about 160° C. and melt mixing for a further 5 minutes.

The results of testing the materials after curing for 8 minutes at about 160° C. are provided in Table 2. The tear initiation and total tear energy are determined from tear specimen ASTM D624-C.

TABLE 2

| | Comparative 2 | Example 2 |
|---|---|---|
| Tensile Stress at Break (MPa) | 18.8 | 20.6 |
| Tensile Elongation to Break % | 500 | 520 |
| Tear Initiation Energy (MPa) | 2.9 | 3.7 |
| Total Tear Energy (MPa) | 3.3 | 4.2 |

The above table 2 shows that the example of the invention (prediluted master batch with specific mixing) obtains improved tensile stress at break at over 1.7 MPa, improved tear initiation energy at over 0.7 MPa and including improved total tear energy at over 0.8 MPa versus the comparative example comprising different mixing techniques, proving the utility and inventiveness of the compositions of the invention.

Embodiments

1. A composition comprising a plurality of discrete carbon nanotube fibers having an aspect ratio of from about 25 to about 500, and at least one natural or synthetic elastomer, and optionally at least one filler.
2. The composition of embodiment 1 wherein at least 70 percent, preferably at least 80 percent, by weight of the nanotube fibers are fully exfoliated.
3. The composition of embodiment 1 wherein the nanotube fibers are further functionalized.
4. The composition of embodiment 1 wherein the carbon nanotube fibers comprise an oxidation level from about 3 weight percent to about 15 weight percent.
5. The composition of embodiment 1 wherein the carbon nanotube fibers comprise from about 1 weight percent to about 30 weight percent of the composition.
6. The composition of embodiment 1 in the form of free flowing particles.
7. The composition of embodiment 1 further comprising at least one surfactant or dispersing aid.
8. The composition of embodiment 1 wherein the natural or synthetic elastomer is selected from the group consisting of natural rubbers, polyisobutylene, polybutadiene and styrene-butadiene, butyl rubber, polyisoprene, ethylene propylene diene rubbers and hydrogenated and non-hydrogenated nitrile rubbers, polyurethanes, polyethers, silicones, halogen modified elastomers, especially chloroprene and fluoroelastomers and combinations thereof.
9. The composition of embodiment 1 wherein the fibers are not entangled as a mass.
10. A process to form a carbon nanotube fiber/elastomer composite comprising the steps of:
    (a) selecting discrete carbon nanotube fibers having an aspect ratio of from 25 to 500,
    (b) blending the fibers with a liquid to form a liquid/fiber mixture,
    (c) optionally adjusting the pH to a desired level,
    (d) agitating the mixture to a degree sufficient to disperse the fibers to form a dispersed fiber mixture,
    (e) optionally combining the dispersed fiber mixture with at least one surfactant,
    (f) combining the dispersed fiber mixture with at least one elastomer at a temperature sufficient to incorporate the dispersed fiber mixture to form a carbon nanotube fiber/elastomer composite/liquid mixture,
    (g) isolating the resulting carbon nanotube fiber/elastomer composite from the liquid.
11. The process of embodiment 10 wherein the carbon nanotube fibers comprise from about 1 to about 30 weight percent of the fiber/elastomer composite of (g).
12. The process of embodiment 10 wherein the liquid is aqueous based.
13. The process of embodiment 10 wherein the agitating step (d) comprises sonication.
14. The process of embodiment 10 wherein the elastomer is selected from the group consisting of natural rubbers, polyisobutylene, polybutadiene and styrene-butadiene rubber, ethylene propylene diene rubbers, butyl rubber, polyisoprene and hydrogenated and non-hydrogenated nitrile rubbers, polyurethanes, polyethers, halogen containing elastomers and fluoroelastomers and combinations thereof.
15. The composition of embodiment 1 further comprising sufficient natural or synthetic elastomer to form a formulation comprising from about 0.1 to about 25 weight percent carbon nanotube fibers.

16. The composition of embodiment 1 in the form of a molded or fabricated article, such as a tire, a hose, a bell, a seal and a tank track.

17. The composition of embodiment 1 further comprising carbon black and/or silica and wherein a molded film comprising the composition has a tensile modulus at 5% strain and 25 degrees C. of at least about 12 MPa.

18. The composition of embodiment 1 further comprising carbon black and/or silica, and wherein a molded film comprising the composition has a tear property at 25 degrees C. of at least about 0.8 MPa.

19. The composition of embodiment 1 further comprising filler, and wherein a molded film comprising the composition has a tensile modulus at 5% strain and 25 degrees C. of at least about 8 MPa.

20. A carbon nanotube fiber/elastomer composite, wherein the carbon nanotube fibers are discrete fibers and comprise from about 10 to about 20 weight percent fibers and wherein the elastomer comprises a styrene copolymer rubber.

21. A method for obtaining individually dispersed carbon nanotubes in rubbers and/or elastomers comprising (a) forming a solution of exfoliated carbon nanotubes at pH greater than or equal to about 7, (b) adding the solution to a rubber or elastomer latex to form a mixture at pH greater than or equal to about 7, (c) coagulating the mixture to form a concentrate, (d) optionally incorporating other fillers into the concentrate, and (e) melt-mixing said concentrate into rubbers and/or elastomers to form elastomeric composites.

22. The method of embodiment 21 wherein the carbon nanotubes comprise less than or equal to about 2% wt of the solution.

23. The method of embodiment 21 wherein the coagulation step (c) comprises mixing with organic molecules of high water solubility such as acetone, denatured alcohol, ethyl alcohol, methanol, acetic acid, tetrahydrofuran that partially or wholly removes surfactants form the latex/carbon nanotube fiber concentrate.

24. The method of embodiment 21 wherein the coagulation step (c) comprises drying, steam stripping or mechanical agitation of the mixture to fully retain surfactants from the latex/carbon nanotube fiber concentrate.

25. The method of embodiment 21 wherein the coagulation step (c) comprises adding a polymeric coagulating agent, preferably polyethylene oxide.

26. The method of embodiment 21 wherein the coagulation step (c) comprises adding at least one acid to the mixture at pH less than or equal to about 4.5 together with at least one monovalent inorganic salt to retain surfactants from the latex/carbon nanotube fiber concentrate.

27. The method of embodiment 21 wherein the mixture or concentrate has a divalent or multivalent metal ion content of less than about 20,000 parts per million.

28. The method of embodiment 21 wherein the mixture or concentrate has a divalent or multivalent metal ion content of less than about 10,000 parts per million.

29. The method of embodiment 21 wherein the mixture or concentrate has a divalent or multivalent metal ion content of less than about 1,000 parts per million.

30. The method of embodiment 21 wherein the coagulation step (c) is such that agglomerations of carbon nanotubes comprise less than 1 percent weight of the concentrate and wherein the carbon nanotube agglomerates comprise more than 10 microns in diameter.

31. An individually dispersed carbon nanotube/rubber or carbon nanotube/elastomer concentrate comprising free flowing particles wherein the concentrate contains a concentration of less than 20,000 parts per million divalent or multivalent metal salt.

32. An individually dispersed carbon nanotube/rubber or carbon nanotube/elastomer concentrate comprising free flowing particles wherein the concentrate contains agglomerations of carbon nanotubes that comprise less than 1 percent by weight of the concentrate and wherein the carbon nanotube agglomerates comprise more than 10 micrometers in diameter.

33. A composite comprising the concentrate of embodiments 31 or 32.

34. A method of dispersing the individually dispersed carbon nanotube/rubber or carbon nanotube/elastomer concentrate into an elastomer by first melt mixing the elastomer and concentrate to a uniform consistency before addition of other fillers and oils.

35. The composition of embodiment 5 comprising a mixture of natural and synthetic elastomers such that each elastomer is compatible with at least one of the elastomers such that the nanotubes are individually dispersed in the mixture of elastomer(s).

36. The composition of embodiment 35 wherein at least one of the elastomers does not comprise nanotubes.

37. A composition comprising one first elastomer and nanotubes, another different second elastomer and nanotubes, and yet another third elastomer which does not comprise nanotubes.

38. A process to increase cure rate of a composition comprising at least one natural or synthetic elastomer and carbon nanotubes, comprising selecting discrete carbon nanotubes to form the cured composition, wherein the cured composition has at least a 25 percent curing rate increase over the curing rate obtained for a cured elastomer not comprising carbon nanotubes.

39. A composition of (A) elastomers, fillers and discrete carbon nanotubes wherein to maintain or increase stiffness or hardness as compared to (B) a composition not containing discrete carbon nanotubes, wherein composition (A) has less filler content than (B).

40. A composition of embodiment 39 wherein 1× parts per hundred elastomer discrete carbon nanotube of composition (A) replaces 5× parts per hundred elastomer or more of the non-carbon nanotube filler of composition (B), where x is 0.1-15.

41. A method of mixing carbon nanotubes and at least one first elastomer, wherein a master batch of carbon nanotubes is first melt mixed with the elastomer, either the same or different from the first elastomer, at a temperature from about 20 to about 200° C., subsequently then additional elastomers, fillers, and additives are added and melt mixed further, to produce a composition suitable for vulcanization.

42. A method of mixing carbon nanotubes and at least one first elastomer, wherein a master batch of carbon nanotubes is first mixed with the elastomer, either the same or different from the first elastomer, at a temperature from about 20 to about 200° C. and in the presence of at least one solvent, then the at least one solvent is removed, subsequently and optionally additional elastomers, fillers and additives are added and mixed further to produce a composition suitable for vulcanization.

43. A method of mixing carbon nanotubes and at least one first elastomer, wherein a master batch of carbon nanotubes is first mixed with the elastomer, either the same or different from the first elastomer, at a temperature from about 20 to about 200° C. and in the presence of at least one solvent, subsequently and optionally additional elastomers, fillers and additives are added and mixed further, followed by solvent removal to produce a composition suitable for vulcanization.

The invention claimed is:

1. A dispersion comprising: a plurality of oxidized, discrete carbon nanotube fibers, wherein the discrete carbon nanotube fibers are open on at least one end, have an aspect ratio of from about 25 to about 500, and are multiwall, and wherein said fibers are present in the range of greater than zero to about 30% by weight based on the total weight of the dispersion wherein the dispersion further comprises water and an additive.

2. The dispersion of claim 1 wherein the additive comprises at least one surfactant or dispersing aid.

3. The dispersion of claim 1 wherein at least 70 percent by weight of the nanotube fibers are fully exfoliated.

4. The dispersion of claim 1 wherein at least 80 percent by weight of the nanotube fibers are fully exfoliated.

5. The dispersion of claim 1 wherein the plurality of oxidized, discrete nanotube fibers fibers comprise an oxidation level from about 0.5 weight percent to about 3 weight percent based on the total weight of discrete carbon nanotubes.

6. The dispersion of claim 1 wherein the oxidized, discrete carbon nanotubes comprise an oxidation species selected from the group consisting of carboxylic acid and derivative carbonyl containing species.

7. The dispersion of claim 1 wherein the additive is selected from the group consisting of a drug molecule, a radiotracer molecule, a radiotherapy molecule, a diagnostic imaging molecule, a fluorescent tracer molecule, a protein molecule, and combinations thereof.

8. The dispersion of claim 1 wherein at least a portion of the additive molecules fit within the interior of the discrete, multi-wall oxidized carbon nanotubes that are open on at least one end.

9. The dispersion of claim 1 wherein the additive has a molecular weight of less than 50,000 Daltons.

10. The dispersion of claim 1 wherein the additive is selected from the group consisting of chemotherapy drugs, cytostatic drugs, and cytotoxic drugs.

11. The dispersion of claim 1 wherein the additive is paclitaxel.

12. A composition comprising: a plurality of oxidized, discrete carbon nanotube fibers, wherein the discrete carbon nanotube fibers are open on at least one end, have an aspect ratio of from about 25 to about 500, and are multiwall, and wherein said fibers are present in the range of greater than zero to about 30% by weight based on the total weight of the composition wherein the composition further comprises water and an additive and wherein the amount of additive is such that greater than about 60 weight percent of the additive is within the interior of the discrete, multi-wall oxidized carbon nanotube fibers that are open on at least one end.

13. The composition of claim 12 wherein at least 70 percent by weight of the carbon nanotube fibers are fully exfoliated.

14. The composition of claim 12 wherein the amount of additive is such that greater than about 99 weight percent of the additive is within the interior of the discrete, multi-wall oxidized carbon nanotube fibers that are open on at least one end.

15. The composition of claim 12 wherein the oxidized, discrete carbon nanotube fibers comprise an oxidation species selected from the group consisting of carboxylic acid and derivative carbonyl containing species.

16. The composition of claim 12 wherein the additive is selected from the group consisting of a drug molecule, a protein molecule, and combinations thereof.

17. The composition of claim 16 which further comprises a compound selected from, a radiotracer molecule, a radiotherapy molecule, a diagnostic imaging molecule, a fluorescent tracer molecule, sodium dodecyl sulfate, cetyltrimethyl ammonium bromide, a polyvinyl alcohol, a polyalkylene oxide, a carboxymethyl cellulose, polyglycolic acid, polyacrylic acid, and polylactic acid, polyvinylpyrrolidone, a peptide, an amino acid, a protein, a polysaccharide, and mixtures thereof.

18. The composition of claim 12 wherein the amount of additive is such that greater than about 70 weight percent of the additive is within the interior of the discrete, multi-wall oxidized carbon nanotube fibers that are open on at least one end.

19. The composition of claim 12 wherein the amount of additive is such that greater than about 80 weight percent of the additive is within the interior of the discrete, multi-wall oxidized carbon nanotube fibers that are open on at least one end.

20. The composition of claim 19 wherein the additive has a hydrodynamic radius smaller than the average diameter of the nanotube opening.

* * * * *